US008926551B2

(12) United States Patent
Lo et al.

(10) Patent No.: US 8,926,551 B2
(45) Date of Patent: Jan. 6, 2015

(54) PERITONEAL DIALYSIS THERAPY WITH LARGE DIALYSIS SOLUTION VOLUMES

(75) Inventors: Ying-Cheng Lo, Green Oaks, IL (US); Alp Akonur, Evanston, IL (US); Yuanpang S. Ding, Libertyville, IL (US)

(73) Assignees: Baxter Healthcare Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 879 days.

(21) Appl. No.: 12/498,853

(22) Filed: Jul. 7, 2009

(65) Prior Publication Data

US 2011/0009810 A1    Jan. 13, 2011

(51) Int. Cl.
    *A61M 1/00* (2006.01)
    *A61M 1/28* (2006.01)

(52) U.S. Cl.
    CPC .................................. *A61M 1/28* (2013.01)
    USPC .......... 604/29; 604/5.04; 604/6.09; 604/6.11; 604/28; 210/645; 210/646; 700/282

(58) Field of Classification Search
    USPC ........... 604/29, 5.04, 6.09, 6.11, 28; 210/645, 210/646; 700/282
    See application file for complete search history.

(56) References Cited

U.S. PATENT DOCUMENTS

| | | | |
|---|---|---|---|
| 4,008,712 A | 2/1977 | Nyboer et al. | |
| 4,016,868 A | 4/1977 | Allison et al. | |
| 4,192,748 A | 3/1980 | Hyden | |
| 4,204,545 A | 5/1980 | Yamakoshi | |
| 4,244,787 A | 1/1981 | Klein et al. | |
| 4,301,879 A | 11/1981 | Dubow | |
| 4,318,447 A | 3/1982 | Northcutt | |
| 4,338,190 A | 7/1982 | Kraus et al. | |
| 4,370,983 A | 2/1983 | Lichtenstein | |
| 4,508,622 A | 4/1985 | Polaschegg et al. | |
| 4,586,920 A | 5/1986 | Peabody | |
| 4,618,343 A | 10/1986 | Polaschegg | |
| 4,620,846 A | 11/1986 | Goldberg et al. | |
| 4,629,015 A | 12/1986 | Fried et al. | |

(Continued)

FOREIGN PATENT DOCUMENTS

| EP | 0013334 | 7/1980 |
|---|---|---|
| EP | 0121085 | 10/1984 |

(Continued)

OTHER PUBLICATIONS

Vonesh E. F., Story K, O'Neill WT for the PD ADEQUEST International Study Group. Perit Dial Int 1999; 19:556-571.

(Continued)

*Primary Examiner* — Quynh-Nhu H Vu
*Assistant Examiner* — Larry R Wilson
(74) *Attorney, Agent, or Firm* — K&L Gates LLP

(57) ABSTRACT

Patients suffering from acute renal failure must be diagnosed and treated quickly so that a physician can confidently prescribe either peritoneal dialysis or hemodialysis. In one way of quickly treating the patients, software is used to calculate a suitable peritoneal dialysis prescription without regard to how short or how long a dialysis cycle is used, and without regard to a total dialysate fluid volume for a therapy. For patients with suitable peritoneal membrane transport properties, the software program suggests that, at least over a short period of time, unexpectedly high ultrafiltrate volumes and high clearances may be achieved.

20 Claims, 8 Drawing Sheets

(56) References Cited

U.S. PATENT DOCUMENTS

| | | | |
|---|---|---|---|
| 4,869,286 A | 9/1989 | Williams et al. | |
| 4,895,657 A | 1/1990 | Polaschegg | |
| 4,915,688 A | 4/1990 | Bischof et al. | |
| 5,004,459 A | 4/1991 | Peabody et al. | |
| 5,063,937 A | 11/1991 | Ezenwa et al. | |
| 5,083,872 A | 1/1992 | Farling et al. | |
| 5,091,094 A | 2/1992 | Veech | |
| 5,141,327 A | 8/1992 | Shiobara | |
| 5,152,743 A | 10/1992 | Gorsuch et al. | |
| 5,247,434 A | 9/1993 | Peterson et al. | |
| 5,261,876 A | 11/1993 | Popovich et al. | |
| 5,311,899 A | 5/1994 | Isayama et al. | |
| 5,326,476 A | 7/1994 | Grogan et al. | |
| 5,344,392 A | 9/1994 | Senniger et al. | |
| 5,360,013 A | 11/1994 | Gilbert | |
| 5,374,813 A | 12/1994 | Shipp | |
| 5,401,238 A | 3/1995 | Pirazzoli | |
| 5,442,969 A | 8/1995 | Troutner et al. | |
| 5,449,000 A | 9/1995 | Libke et al. | |
| 5,508,912 A | 4/1996 | Schneiderman | |
| 5,518,623 A | 5/1996 | Keshaviah et al. | |
| 5,540,265 A | 7/1996 | Polaschegg et al. | |
| 5,567,320 A | 10/1996 | Goux et al. | |
| 5,572,992 A | 11/1996 | Kankkunen et al. | |
| 5,580,460 A | 12/1996 | Polaschegg | |
| 5,583,948 A | 12/1996 | Shibayama | |
| 5,608,193 A | 3/1997 | Almogaibil | |
| 5,643,201 A | 7/1997 | Peabody et al. | |
| 5,654,537 A | 8/1997 | Prater | |
| 5,670,057 A | 9/1997 | Chen et al. | |
| 5,671,362 A | 9/1997 | Cowe et al. | |
| 5,725,773 A | 3/1998 | Polaschegg | |
| 5,733,442 A | 3/1998 | Shukla | |
| 5,735,284 A | 4/1998 | Tsoglin et al. | |
| 5,744,031 A | 4/1998 | Bene | |
| 5,752,234 A | 5/1998 | Withers | |
| 5,778,643 A | 7/1998 | Tacchini | |
| 5,788,846 A | 8/1998 | Sternby | |
| 5,800,397 A | 9/1998 | Wilson et al. | |
| 5,912,818 A | 6/1999 | McGrady et al. | |
| 5,925,011 A | 7/1999 | Faict et al. | |
| 5,925,014 A | 7/1999 | Teeple, Jr. | |
| 5,954,951 A | 9/1999 | Nuccio | |
| 5,997,502 A | 12/1999 | Reilly et al. | |
| 6,017,318 A | 1/2000 | Gauthier et al. | |
| 6,081,786 A | 6/2000 | Barry et al. | |
| 6,228,033 B1 | 5/2001 | Kööbi et al. | |
| 6,228,047 B1 * | 5/2001 | Dadson | 604/29 |
| 6,246,894 B1 | 6/2001 | Steuer et al. | |
| 6,247,840 B1 | 6/2001 | Gaffar | |
| 6,385,593 B2 | 5/2002 | Linberg | |
| 6,615,077 B1 | 9/2003 | Zhu et al. | |
| 6,685,831 B2 | 2/2004 | Dönig et al. | |
| 6,733,676 B2 | 5/2004 | Takai | |
| 6,835,175 B1 | 12/2004 | Porumbescu | |
| 6,881,344 B2 | 4/2005 | Vasta et al. | |
| 6,882,982 B2 | 4/2005 | McMenimen et al. | |
| 6,925,447 B2 | 8/2005 | McMenimen et al. | |
| 6,979,309 B2 | 12/2005 | Burbank et al. | |
| 7,076,303 B2 | 7/2006 | Linberg | |
| 7,115,113 B2 | 10/2006 | Evans et al. | |
| 7,142,118 B2 | 11/2006 | Hamilton et al. | |
| 7,153,286 B2 | 12/2006 | Busby et al. | |
| 7,208,092 B2 | 4/2007 | Micheli | |
| 7,214,210 B2 | 5/2007 | Kamen et al. | |
| 7,225,030 B2 | 5/2007 | Kroll et al. | |
| 7,228,170 B2 | 6/2007 | Zhu et al. | |
| 7,230,521 B2 | 6/2007 | Terenna | |
| 7,252,230 B1 | 8/2007 | Sheikh et al. | |
| 7,303,541 B2 | 12/2007 | Hamada et al. | |
| 7,801,591 B1 | 9/2010 | Shusterman | |
| 2002/0082728 A1 | 6/2002 | Mueller et al. | |
| 2002/0103453 A1 | 8/2002 | Burbank et al. | |
| 2004/0092841 A1 | 5/2004 | Singer | |
| 2004/0111293 A1 | 6/2004 | Firanek et al. | |
| 2004/0111294 A1 | 6/2004 | McNally et al. | |
| 2005/0256745 A1 | 11/2005 | Dalton | |
| 2006/0015015 A1 | 1/2006 | Kawamoto et al. | |
| 2007/0112297 A1 | 5/2007 | Plahey et al. | |
| 2008/0082582 A1 | 4/2008 | Jung et al. | |
| 2008/0125693 A1 | 5/2008 | Gavin et al. | |
| 2008/0161751 A1 | 7/2008 | Plahey et al. | |
| 2009/0095679 A1 | 4/2009 | Demers et al. | |
| 2009/0275881 A1 | 11/2009 | Lo et al. | |
| 2009/0275883 A1 | 11/2009 | Chapman et al. | |

FOREIGN PATENT DOCUMENTS

| | | |
|---|---|---|
| EP | 0311848 | 4/1989 |
| EP | 0575970 | 12/1993 |
| EP | 0 621 046 | 10/1994 |
| EP | 0650739 | 5/1995 |
| EP | 0 711 569 | 5/1996 |
| EP | 1205144 | 5/2002 |
| EP | 1277485 | 1/2003 |
| EP | 1535576 | 6/2005 |
| EP | 1623731 | 2/2006 |
| EP | 1938849 | 7/2008 |
| FR | 2 696 644 | 4/1994 |
| GB | 2069706 | 8/1981 |
| GB | 2135598 | 9/1984 |
| JP | 57161511 | 10/1982 |
| JP | 2000/271127 | 10/2000 |
| JP | 2003/047657 | 2/2003 |
| WO | 82/04127 | 11/1982 |
| WO | WO92/11046 | 7/1992 |
| WO | WO92/19153 | 11/1992 |
| WO | WO96/25214 | 8/1996 |
| WO | WO96/32883 | 10/1996 |
| WO | WO98/51211 | 11/1998 |
| WO | WO02/13691 | 2/2002 |
| WO | WO03/063929 | 8/2003 |
| WO | WO2005/035023 | 4/2005 |
| WO | WO2008/008281 | 1/2008 |

OTHER PUBLICATIONS

Heimburger O, Waniewski J. Ultrafiltration Failure in Peritoneal Dialysis Patients. Perit Dial Int 2004; 24:506-508.

Mujais S, Nolph K, Gokal R, et al. Evaluation and Management of Ultrafiltration Problems in Peritoneal Dialysis. Perit Dial Int 2000; 20:S4, S5-21.

Abu-Alfa AK, Burkhard J, Piraino b, Pulliam J, Mujais S. Approach to Fluid Management in Peritoneal Dialysis: A Practical Algorithm. Kidney Int 2002; 62:S81 S8-S16.

La Milia V, Di Filippo, Crepaldi M et al. Mini-Peritoneal Equilibration Test: A Simple and Fast Method to Assess Free Water and Small Solute Transport Across the Peritoneal Membrane. Kidney Int 2005; 68:840-846.

Blake P. Individualized Prescription of Peritoneal Dialysis Therapy. Peritoneal Dialysis International, vol. 19, Supp. 2, 1999.

Brunkhorst R. Individualized PD Prescription: APD Versus CAPD. Peritoneal Dialysis International, vol. 25, Supp. 3, 2005.

Rippe B. et al. Computer Simulation of Peritoneal Fluid Transport in CAPD. Kidney International, vol. 40 (1991), pp. 315-325.

Waniewski J. Mathematical Modeling of Fluid and Solute Transport in Hemodialysis and Peritoneal Dialysis. J. of Membrane Science 274 (2006), 24-37.

Vonesh E. et al. Kinetic Modeling as a Prescription Aid in Peritoneal Dialysis. Blood Purif 1991; 9: 246-270.

Prowant BF, Schmidt LM. The Peritoneal Equilibration Test: A Nursing Discussion. *Anna J.* 1991; 18:361-366.

Schmidt LM, Prowant BF. How to do a Peritoneal Equilibration Test. *ANNA J.* 1991; 18: 368-370.

Twardowski ZJ, Nolph KD, Khanna R, et al. Peritoneal Equilibration Test. *Perit Dial Bull.* 1987; 7:138-147.

Twardowski ZJ, Clinical Value of Standardized Equilibration Tests in CAPD patients. *Blood Purif.* 1989; 7:95-108.

Twardowski ZJ, Prowant BF, Moore HL, Lou LC, White E, Farris K. Short Peritoneal Equilibration Test: Impact of Preceding Dwell Time. *Adv Perit Dial.* 2003: 19:53-58.

(56) References Cited

OTHER PUBLICATIONS

Lilaj T, Dittrich E, Puttinger H, et al. A Preceding Exchange with Polyglucose Versus Glucose Solution Modifies Peritoneal Equilibration Test Results. *Am J Kidney Dis.* 2001; 38:118-126.

Adcockl A., Fox K., Walker P., and Raymond K., Clinical Experience and Comparative Analysis of the Standard and Fast Peritoneal Equilibration Tests (PET), Advances in PD, vol. 8: 59-61, 1992.

Pannekeet et al., The standard peritoneal permeability analysis: A tool for the assessment of peritoneal permeability characteristics in CAPD patients, Kidney Int. 1995; 48:866-875.

Vonesh E. F. and Rippe B., Net fluid absorption under membrane transport models of peritoneal dialysis, Blood Purif 1992; 10:209-226.

Passadakis P. and Oreopoulos D. G., Peritoneal Dialysis in Patients with Acute Renal Failure, Advances in Peritoneal Dialysis, vol. 23, 7-16, 2007.

Akonur, et al. Ultrafiltration Efficiency During Automated Peritoneal Dialysis Using Glucose-Based Solutions, Advances in Peritoneal Dialysis, vol. 24, 69-74, 2008.

La Milia et al. Simultaneous measurement of peritoneal glucose and free water osmotic conductances, Kidney International vol. 72, 643-650, 2007.

Agrawal and Nolph Advantages of ATidal Peritoneal Dialysis, Peritoneal Dialysis International, vol. 20, S98-S100, 2000.

Article entitled: "A Practicle Solution for Clinical and Quality Assurance"; written by Gambro (article undated).

Michael F. Flessner article entitled: "Computerized Kinetic Modeling: A New Tool in the Quest for Adequacy in Peritoneal Dialysis"; Peritoneal Dialyssi International, vol. 17, pp. 581-585 (1997).

Gambro PDC Measuting in APD Patient Manual written by Gambro Lundia AB, Lund, Sweden, Oct. 1998, printed by Elanders Skogs Grafiska AB, Rev. 3, Jan. 2001.

Gambro Laboratoriesvar APD written by Gambro Lundia AB, Lundia AB, Lund, Sweden, Jan. 1999, printed by Elanders Skogs Grafiska AB, Rev. 2, May 2001.

Gambro PDC—Personal Dialysis Capacity [online] [retrieved Nov. 10, 2006]. Retrieved from the Internet at <URL: http://www.em.gambro.com/Pages/InfoPage.aspx?id=4788.html>.

Baxter RENALSOFT Patient Management Software Suite description [online] [retrieved Aug. 21, 2008, available prior to Jul. 9, 2008]. Retrieved from the Internet at <URL: http://www.baxter.com/products/renal/software/renalsoft.html>.

Search Report dated Dec. 21, 2009—PCT/US2009/050056.

International Search Report and the Written Opinion for International Application No. PCT/US2009/050050 dated May 3, 2010.

International Search Report and the Written Opinion for International Application No. PCT/US2009/050066 dated May 3, 2010.

International Search Report and the Written Opinion for International Application No. PCT/US2009/050073 dated May 3, 2010.

International Search Report and Written Opinion for International Application No. PCT/US2010/037082 mailed on Aug. 31, 2010.

Notification of Transmittal of the International Preliminary Report on Patentability for International Application No. PCT/US2009/050050 dated Oct. 5, 2010.

Notification of Transmittal of the International Preliminary Report on Patentability for International Application No. PCT/US2009/050066 dated Oct. 12, 2010.

Notification of Transmittal of the International Preliminary Report on Patentability for International Application No. PCT/US2009/050073 dated Oct. 12, 2010.

Notification of Transmittal of the International Preliminary Report on Patentability for International Application No. PCT/US2009/050056 dated Oct. 15, 2010.

* cited by examiner

PERITONEAL DIALYSIS THERAPY WITH LARGE DIALYSIS SOLUTION VOLUMES

RELATED APPLICATION

The present application is related to U.S. application Ser. No. 12/498,847, Simplified Peritoneal Equilibration Test for Peritoneal Dialysis, which was filed concurrently with the present application.

BACKGROUND

The present disclosure relates generally to medical fluid delivery systems and methods. This disclosure includes systems and methods for calculating a peritoneal dialysis therapy that will yield one or more favorable outcomes for a patient. In particular, the disclosure concerns calculating a series of dialysis outcomes using a series of dialysis variables with a digital computer and a computer program.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue. Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

Peritoneal dialysis machines are used to accomplish this task. Such machines are described, for example, in the following U.S. patents, all of which are incorporated by reference in their entirety, as though each patent were set forth herein, page by page, in its entirety: U.S. Pat. Nos. 5,350,357; 5,324,422; 5,421,823; 5,431,626; 5,438,510; 5,474,683; 5,628,908; 5,634,896; 5,938,634; 5,989,423; 7,153,286; and 7,208,092.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement. In particular there is room for improvement in the selection of dwell times for the patient.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. These systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia.

The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to control ultrafiltration, which is the process by which water (with electrolytes and other neutral solutes) moves across a membrane, such as a dialyzer or peritoneal membrane. For example, ultrafiltration in peritoneal dialysis is a result of osmotic and hydrostatic pressure differences between blood and dialysate across the patient's peritoneal membrane. It is also important to control the concentration of metabolic substances in the patient's bloodstream, such as urea concentration, $\beta_2$-microglobulin, creatinine concentration, and so forth. Each of these, along with many other variables, constitutes a peritoneal dialysis outcome.

Each patient is different, possessing for instance, a unique peritoneal membrane, its own separation characteristics, and its unique response to peritoneal dialysis. Each patient is also different with respect to body surface area (BSA) and total body water volume, which also have an effect on transport characteristics. Each patient is different in terms of transport characteristics that relate to the ultrafiltration rate. Each patient is also different in terms of response to dialysis, that is, the amount of water and waste removed in a given time period, using a given fill volume, a particular dialysis fluid, and so forth.

One basic difference among patients is the rate at which water and metabolic wastes pass from the patient's bloodstream through the peritoneal membrane. Once the water and wastes pass through the peritoneal membrane, they are absorbed into the dialysis therapy fluid that has been placed into the patient's peritoneal cavity, and then removed from the patient. A peritoneal equilibration test (PET) determines the relative rate of transmembrane transport. Patients can then be classified as high-rate transporters, high-average transporters, low-average transporters, or low-rate transporters, depending on the speed of waste removal and absorption of glucose from the dialysis fluid. Other user classes may also be used, such as high, average, and low transporters. Patients may also be classified in terms of their total body surface area ("BSA"), which depends only on the height and weight of the patient.

In general, the rate of water removal is different from the rate of waste removal, and both depend on the patient transporter type and is indirectly related to patient membrane transport type. For example, fast transporters can quickly pass metabolic waste, but glucose from the dialysis solution is rapidly absorbed into the body. As a result, glucose concentration in the dialysate decreases and the osmotic gradient or driving force diminishes within a variable period of time, depending on the patient transporter type. Thus, high transporters may benefit more from shorter dwell times, such as those used in automated peritoneal dialysis (APD), where the effect of high osmotic gradients is still present.

Conversely, the osmotic gradient will be sustained for a longer period of time in the case of a low transporter patient, resulting in a larger volume of ultrafiltrate removal. Such a patient will likely benefit from a longer dwell time, such as a continuous ambulatory peritoneal dialysis (CAPD) and with perhaps only a single nighttime exchange. Much useful information about a patient's response to therapy can be learned from administering the PET to the patient. The results of the PET can then be used to prescribe the therapy that would lead to the best outcome for that patient.

However, present PET tests require long periods of time to administer and also typically require at least one blood sample for confirmation of the level of certain waste products in the patient's blood, such as creatinine, to be sure that dialysis therapy being administered is indeed effective. Thus, while the PET test can be valuable in deciding the general characteristics of a patient, the difficulty in administering a PET test may be a significant barrier in determining the therapy best suited for a patient.

This may be particularly true in a patient suffering from unplanned or acute renal failure. Acute renal failure can occur in an emergency situation, such as a car accident, in which the patient loses renal function. In these cases, it is clear that the patient is suffering and requires dialysis quickly. Without some guidance on which peritoneal dialysis treatment to use, such a patient may be prematurely routed to hemodialysis rather than more convenient and less costly peritoneal dialysis. What is needed is a better way to select a peritoneal dialysis therapy that is suited to a patient that needs dialysis in an unplanned situation.

SUMMARY

One embodiment of the present disclosure is a method of calculating a peritoneal dialysis therapy. The method includes steps of inputting data of a patient and selecting a fill volume for a cycle of the peritoneal dialysis therapy, and also selecting at least one therapy parameter or at least one desired outcome of the peritoneal dialysis therapy. The method also includes a step of calculating a therapy for the patient using a digital computer, wherein the therapy is calculated without regard to values of at least one of a therapy volume and a cycle time.

Another embodiment of the present disclosure is a computer program on a computer readable medium for calculating a peritoneal dialysis therapy. The computer program includes logic for accepting input data for a patient and logic for accepting a fill volume for a cycle of the peritoneal dialysis therapy. The program also includes logic for accepting an input of at least one dialysis therapy parameter or an input of at least one desired outcome of the peritoneal dialysis therapy. The program also includes logic for calculating a therapy for the patient using the inputs and a digital computer, wherein the therapy is calculated without regard to values of at least one of a therapy volume and a cycle time.

A further embodiment of the present disclosure is a method for calculating a peritoneal dialysis therapy. The method includes steps of inputting data of a patient and selecting at least one input parameter for the peritoneal dialysis therapy. The method also includes steps of selecting a fill volume for a cycle of the peritoneal dialysis therapy and calculating at least one peritoneal dialysis therapy including at least one outcome of the therapy for the patient using a digital computer, wherein the therapy is calculated without regard to values of at least one of a therapy volume and a cycle time.

Still another embodiment of the present disclosure is a computer program on a computer readable medium for calculating a peritoneal dialysis therapy. The computer program includes logic for accepting input data for a patient and logic for accepting at least one input parameter of the peritoneal dialysis therapy. The program also includes logic for accepting a fill volume for a cycle of the peritoneal dialysis therapy and for calculating at least one peritoneal dialysis therapy including at least one outcome of the therapy for the patient using a digital computer, wherein the therapy is calculated without regard to values of at least one of a therapy volume and a cycle time.

Embodiments of the present disclosure are unexpected and useful because they point to shorter peritoneal dialysis cycle times and higher dialysis therapy volumes as ways to help patients. These methods can be used to advantage for patients that experience unplanned or acute kidney disease. They may also be used to advantage for faster and greater relief of patients presently utilizing peritoneal dialysis, especially patients with high transporter peritoneal dialysis membranes.

Additional features and advantages are described herein, and will be apparent from the following Detailed Description and the figures.

DETAILED DESCRIPTION

Peritoneal equilibration tests date back to the work of Zyblut Twardowski et al. in *Peritoneal Equilibration Test, Perit. Dial Bull*, 7 (3), pp. 138-47 (1987) (hereinafter "Zyblut 1987"), and *Clinical Value of Standardized Equilibration Tests in CAPD Patients. Blood Purif*, 7, pp. 95-108 (1989). This work, and much work that followed, may be generally summarized with FIG. 1, which graphs on the abscissa or x-axis the ratio of $D/D_0$, the ratio of a concentration of glucose in the used dialysis fluid to the initial concentration of glucose in the fresh dialysis fluid. The graph also presents on the ordinate or y-axis the ratio of the concentration of creatinine in the used dialysate to the concentration of creatinine in the plasma, the ratio D/P, that is, in the concentration in the spent dialysis fluid to the concentration in the patient's blood plasma.

Figure 1:
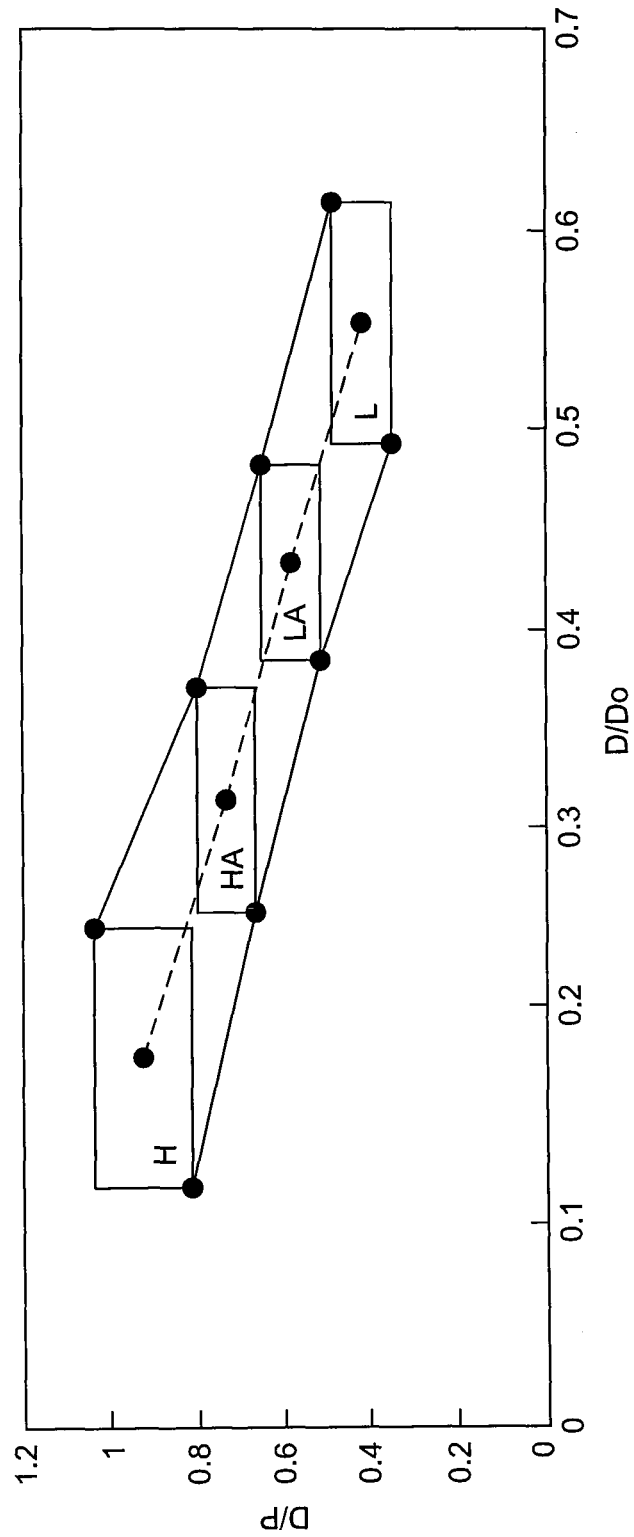
FIG. 1 is a prior art depiction of patient membrane categories.

Dialysis patients, or indeed the general population, may be classified by the transport characteristics of their peritoneal membrane into one of four categories, as shown in FIG. 1. "High" or "H" transporters have a higher ratio of a concentration of waste-product solute in the dialysate fluid to that in their blood, and a lower ratio of glucose in the dialysis fluid to the initial concentration of glucose in the dialysis fluid, when compared to "low" or "L" transporters. Patients with intermediate transport characteristics may be classified as "high-average" or "HA" transporters, or "low-average" or "LA" transporters. In simpler terms, high transporters move the solutes through their peritoneum faster and achieve a higher D/P ratio, but glucose in the dialysis fluid also transports rapidly, and thus there is a lower ratio of glucose to initial glucose ($D/D_0$) in the spent dialysis fluid. Low transporters move the solutes through their peritoneum more slowly, but achieve higher ratios of solute in the spent dialysis fluid as compared with an initial value of the solute in the dialysis fluid. High-average and low-average transporters are intermediate between these two.

In prescribing a therapy for high transporters, it is clear that a therapy should involve greater amounts of dialysis fluid and shorter dwell times for higher ultrafiltrate. For low transporters, lesser amounts of dialysis fluid may be combined with longer dwell times to achieve both higher ultrafiltration and more solute removal.

FIG. 1 is a summary chart that leaves off much of the details in how these charts were prepared. As is well known to those with ordinary skill in the art, these charts are actually first constructed as time-scales, with time plotted on the abscissa and $D/D_0$ or D/P plotted on the ordinate. See Zyblut 1987. The ratio of $D/D_0$ and D/P may then be plotted, leaving out the time element. The result is an elegant solution that appears to neatly categorize patients.

In practice, a standard PET may involve an entire eight to twelve hour night exchange with 3.86% or 2.27% glucose solution preceding the test exchange, if it includes a kinetic analysis of the patient's membrane. This is not strictly necessary to determine the patient's membrane transport status. One technique is to then drain the abdomen completely over a twenty-minute period, and then infuse about two liters of 2.27% glucose over a ten-minute period. To obtain the initial sample, the patient is turned side to side and 200 ml is drained immediately after infusion, including a ten-ml sample for glucose, urea and creatinine. The remaining 190 ml is then returned for the dwell and this sampling procedure is repeated at several intervals, such as thirty minutes, one hour, two hours and three hours, each with a drain and a subsequent two-liter infusion. After the two hour sample is taken, a blood sample is also taken for tests for blood urea nitrogen ("BUN") and creatinine. A final infusion and dwell is taken at the four-hour mark, followed by a drain and a measurement of total effluent volume.

Once the above measurements are taken, the $D/D_0$ glucose and D/P creatinine results are used in a chart similar to those described above to classify the patient's peritoneal membrane in one of the four categories. This procedure takes a long time to accomplish and does not quickly yield the desired results.

Since 1989, many attempts have been made to devise faster PET tests, but the method described above is still widely accepted and applied to assess peritoneal membrane function for peritoneal dialysis patients. Adcock et al. suggested a faster method in which the initial glucose concentration and other intermediate samples were not measured, and used only the plasma sample and the last, four-hour time point. Adcock et al., *Clinical Experience and Comparative Analysis of the Standard and Fast Peritoneal Equilibration Tests (PET)*, Advances in Peritoneal Dialysis, vol. 8, pp. 59-61 (1992). La Milia suggested a method in which the standard four-hour dwell is replaced with a one hour dwell using a 3.86% glucose solution, but still required the blood sample. La Milia et al., *Mini Peritoneal Equilibration Test: A simple and fast method to assess free water and small solute transport across the peritoneal membrane*, Kidney Int'l 68, pp. 840-846 (2005).

Figure 2:
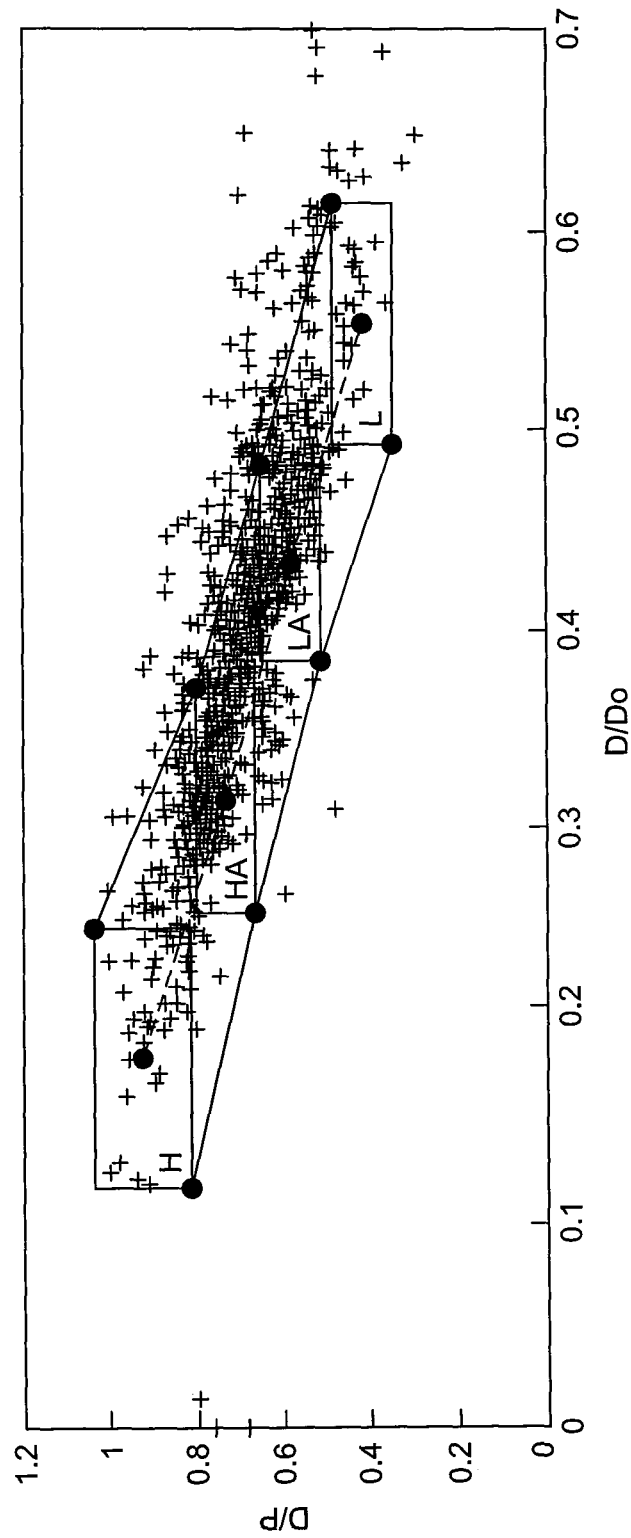
FIG. 2 is a graph of how the prior art fails to adequately place patients among the categories

The reality of classification schemes, however, is better depicted in FIG. 2. In studying about one-thousand patients for whom clinical data are available, it has been unexpectedly discovered that the above tests and the accepted categories do not correctly categorize about 40% of patients. FIG. 2 depicts the results of the survey for both the D/P and the $D/D_0$ axes. These data depict results using a standard PET as described above. Approximately 40% of the patient thus do not fit into any of the four categories. Another way of saying this is that the long and involved PET procedure described above does not correctly classify about half of all patients. It is expected that the shorter PET's discussed above will also misclassify or fail to classify at least about that percentage of patients.

Improved Procedure for PET

The present disclosure describes a new test, the simplified peritoneal equilibration test ("S-PET"), that is less labor intensive and uses what may be described as more effective sampling. The present disclosure also includes a variant of the S-PET, a "fast" peritoneal equilibration test ("F-PET"), as explained below. A peritoneal dialysis machine, such as a HomeChoice® dialysis machine, is helpful in administering the test. In this test, samples of the dialysis fluid are taken for analysis of urea, creatinine and glucose content. No blood sample is taken and either 2.27% glucose (Dianeal™ 2.27%) or 3.86% glucose (Dianeal™ 3.86%) dialysis solution may be used. Measurements may be taken initially, at thirty minutes and at the one, two and four hour marks. Based on these tests, an estimate for a curve-fit is made for a final creatinine concentration in the dialysis fluid. Tests may instead be based on only two or three readings, such as readings at four hours and eight hours, for example, or tests taken at one hour, two hours and eight hours. The reading at the start of the test may be taken as zero, for example, to spare the patient the discomfort and labor in taking what is likely the least-useful test. Alternatively, other time points may be used.

FIGS. 3A to 3D depict graphically the result of tests for creatinine for the four categories of patients, including a blood sample. Each of the graphs displays creatinine concentration test results plotted against the time period after infusion of the dialysis fluid. Each graph also marks a plasma creatinine concentration taken at about two hours. The final point in each graph is an estimate of the equilibrium creatinine concentration for the patient using a standard curve-fitting program, such as Excel™ from Microsoft Corp., Redmond, Wash., U.S.A. or MatLab™ from The MathWorks Inc., Natick, Mass., U.S.A.

Figure 3A:
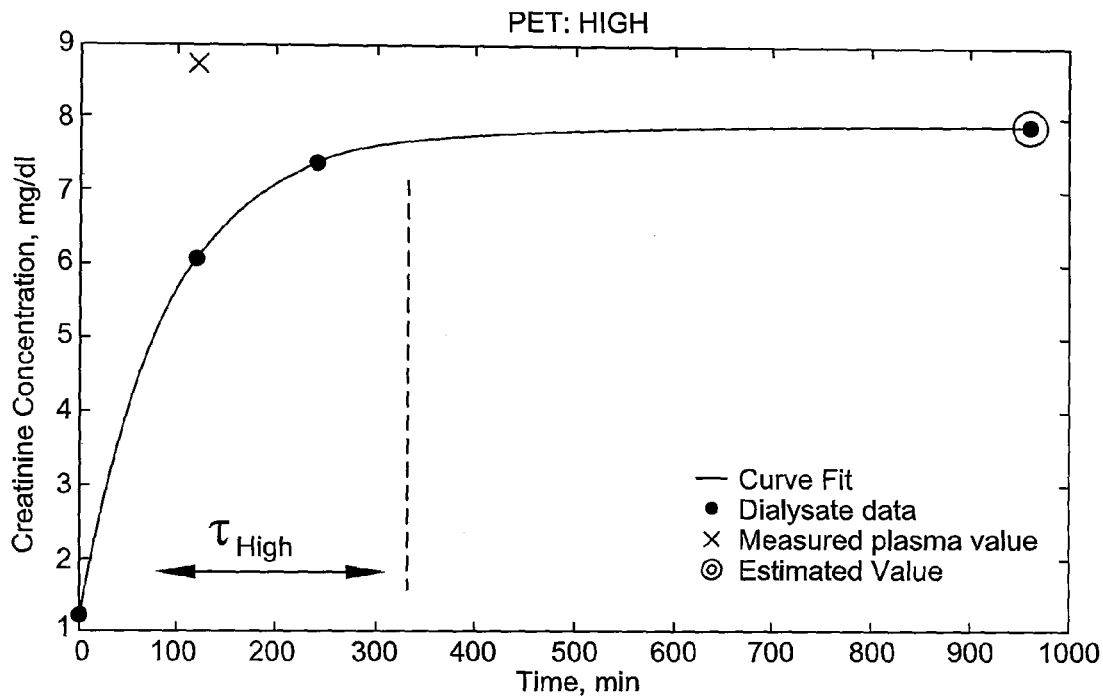
FIGS. 3A to 3D are charts depicting how the fast peritoneal equilibration test uses data to categorize patients by peritoneum transport categories.

In FIG. 3A, the dialysis fluid for a typical high transporter patient is seen to have a rapidly-growing concentration of creatinine. In this category of patients, the creatinine concentration reaches a maximum after about 4 to 5 hours. There is thus no benefit in creatinine removal after a dwell period of about 4 to 5 hours. The test result is achieved simply by infusing the patient and then removing a 10 ml sample at the intervals for which the dots are shown, at the test beginning and after 2 hours and 4 hours. A curve fit is then used to estimate a final or equilibrium concentration for the solute that would be achieved in a very long dwell time. A computer is useful in finding a curve fit for the data. As seen in FIG. 3A, the curve fit is excellent and a final estimate of about 8 mg/dL is very close to the four-hour measurement of about 7.5 mg/dL.

At the time these tests were conducted, a blood plasma sample was also taken at about the 2-hour mark for confirmation. The blood plasma sample for the high-transporter patient had a plasma creatinine concentration of about 8.5 mg/dL at the 2-hour point. The plasma concentration samples taken and displayed at FIGS. 3A to 3D confirm that the plasma concentration is inversely related to membrane transport speed, as expected. That is, as creatinine clearance decreases, more creatinine remains in the patient's blood plasma.

Figure 3B:
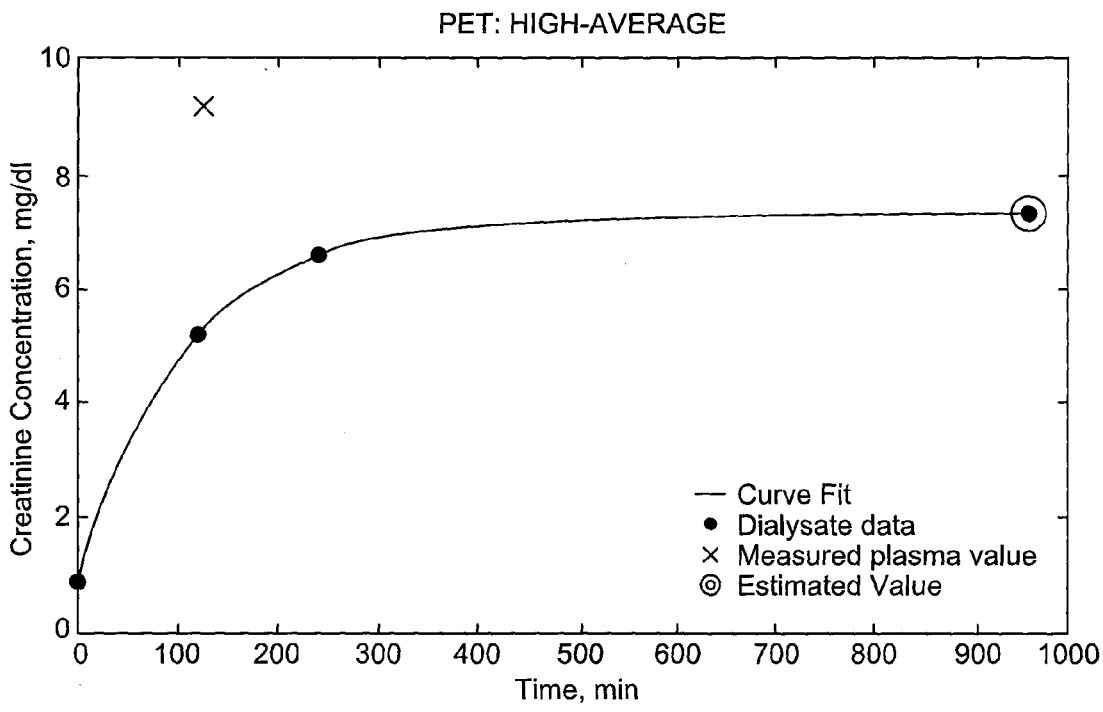

A similar result is seen in FIG. 3B, for patients who may be categorized as high-average transporters, that is, patients whose peritoneal membranes are somewhat less permeable than those of the high transporters. For these patients, the equilibrium concentration of creatinine is estimated at the end of the curve in FIG. 3B at about 7 mg/dL, which is very close to the 4-hour sample concentration of about 6.5 mg/dL. A blood plasma sample showed a creatinine concentration of about 9 mg/dL, a little higher than the high transporter patients, indicating that less creatinine was removed from these patients than from the high transporter patients.

Figure 3C:
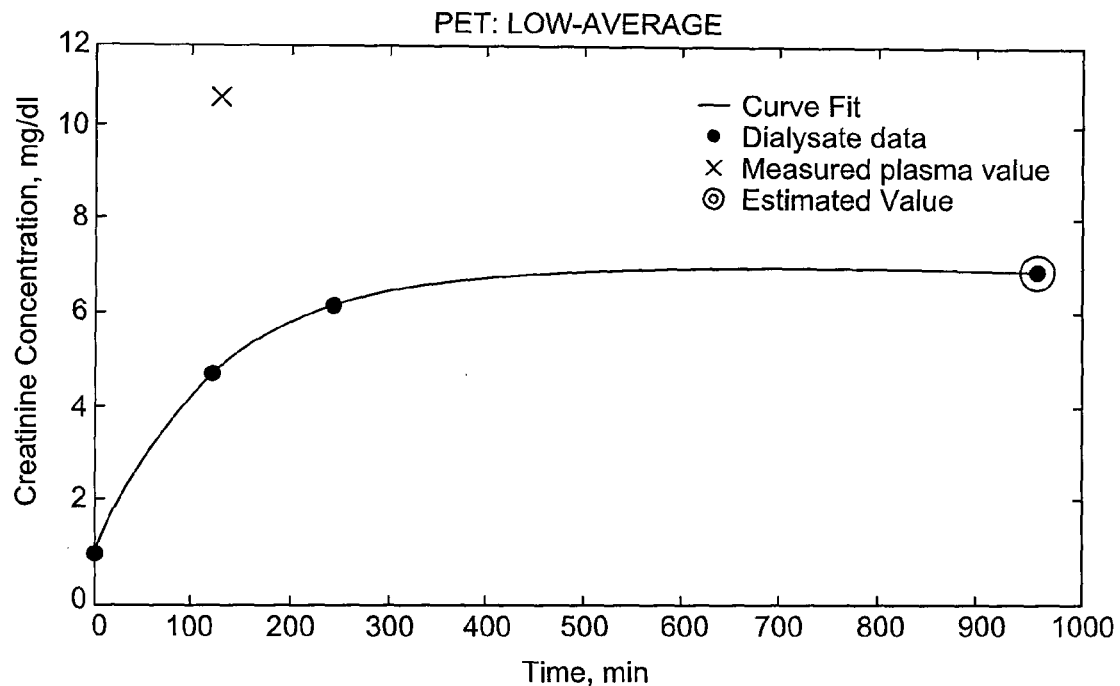

FIG. 3C depicts results for patients with peritoneal membranes that may be categorized as low-average transporters. Creatinine concentration in the 4-hour sample was about 6 mg/dL, a little lower than that shown for the high-average transporters. However, the estimate for the equilibrium creatinine concentration was about 7 mg/dL, very close to that for the high-average transporters. The blood plasma sample shows significantly more creatinine, about 11 mg/dL, compared to high and high-average transporters.

Figure 3D:
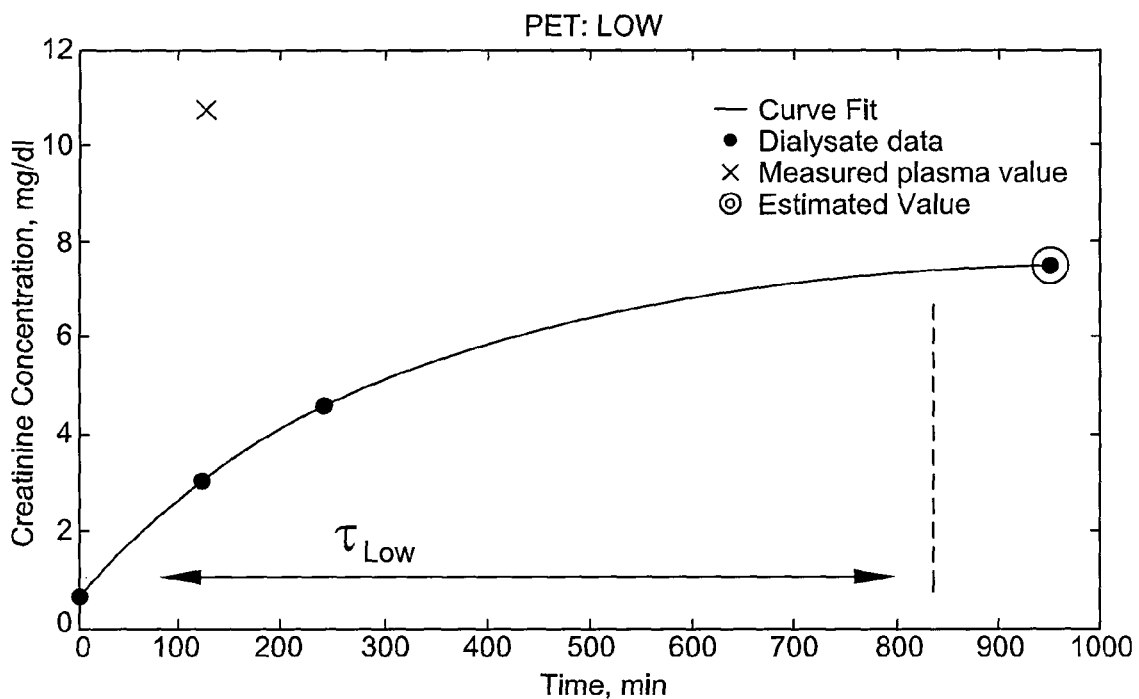

FIG. 3D depicts results for low-transporter patients, that is, those patients whose peritoneal membranes are least amenable to mass transfer. As FIG. 3D depicts, there is no rapid rise in creatinine concentration in the first four hours, compared with the other three categories of transporters. However, the concentration continues to rise over a longer period of time, with an eventual final estimate for the equilibrium concentration of about 7.5 mg/dL, which is close to low-average and high-average transporters. The blood plasma creatinine level at the two-hour mark was about 11 mg/dL, similar to low-average transporters, and significantly higher than patients with membranes classed as either high or high-average. Thus, patients with peritoneal membranes classed as high or high-average are seen to have lower creatinine levels after two hours of dialysis than patients with low or low-average peritoneal membranes.

FIGS. 3A to 3D depict the rise of creatinine levels in spent dialysis fluid. If urea is used as the solute of interest, a similar series of curves would result. Of course, glucose in the dialysis fluid would be expected to decrease, as the glucose is transported from the dialysis fluid across the peritoneal membrane and infuses into the blood of the patient. High transporters would be expected to see a rapid infusion of glucose, while low transporters would expect a slower infusion. Since glucose is the osmotic agent in the dialysis fluid, the loss of glucose from the dialysis fluid lowers its effectiveness in providing the driving force for ultrafiltration.

While conducting this work, it was discovered that the data depicted in FIGS. 3A to 3D may be fit to a curve using the following equation:

$$(CD_t - CD_{eq}) = (CD_0 - CD_{eq})e^{-(t/\tau)},$$

where $CD_t$ is a concentration of the at least one substance at one of the separate times at which dialysis fluid samples are taken, $CD_{eq}$ is an equilibrium concentration of the at least one substance, $CD_0$ is an initial concentration of the at least one substance, t is the time a sample was taken and $\tau$ is an equilibration time constant that is representative of a transport property of a peritoneum or peritoneal membrane of the patient. $CD_{eq}$ and $\tau$ may be estimated using this equation and a curve fit program, based on the measure solute concentrations in the samples taken. The equilibrium concentration of the at least one substance in the dialysis fluid, $CD_{eq}$, is taken as about equal to the concentration of the substance in the blood of the patient, that is, the equilibrium concentration of the solute in both the blood and the dialysis fluid.

In the limited number of patients used in this work, the equilibration time constant for the four categories of transporters were found to be, respectively, 107 minutes, 175 minutes, 242 minutes and 406 minutes, for creatinine for high, high-average, low-average and low transporters, respectively. To determine a final set of numbers, clinical studies with larger numbers of patients should be conducted. Time constants for glucose and urea are expected to be different. In one embodiment, the formula is made part of a computer software program, which is entered into a computer memory or placed onto a medium accessible to a computer for performing calculations necessary to derive the $CD_{eq}$ of the substance.

The test results may be analyzed and graphed in a variety of ways to increase their utility and also to increase the confidence that the new test procedure performs as well as the longer, more arduous traditional PET. Test results from blood plasma urea and creatinine, or other tests, may be used to supplement the results.

Method for Calculating a Peritoneal Dialysis Therapy

While conducting the studies mentioned above for an improved peritoneal equilibration test, additional studies were conducted on how dialysis therapies are prescribed for peritoneal dialysis patients. As is well known to those with skill in dialysis, patient prescriptions are typically calculated using computers with suitable software, such as PDAdequest® or RenalSoft™ from Baxter International Inc., Deerfield, Ill., USA. The computer program may be run in two ways, calculating either an optimal therapy for a patient or a custom therapy for a patient. As is well known to those having skill in this art, calculating a peritoneal dialysis therapy includes calculating the parameters to be used for the therapy, e.g., the materials and methods to be used in the therapy. These parameters may include therapy time and individual cycle times or portions thereof, such as a dwell time. The parameters may also include the concentration of glucose or other osmotic agent in the dialysis fluid. The parameters may also include the type of therapy, such as a tidal therapy, and if so, the percent fill used, e.g., 75% tidal therapy. Note that some materials or methods may be used as inputs to a calculation; in other calculations, the desired outcomes of a dialysis therapy may be specified and the needed inputs, e.g., materials and methods calculated instead.

In an optimal therapy, desired outcomes for a particular patient peritoneal dialysis therapy are input into a program, such as a desired ultrafiltration volume, a target urea clearance, a target creatinine clearance, and so forth. The user also inputs at least a few input parameters, such as a patient fill volume and optionally a glucose concentration or range, and also inputs an identifier for the patient. Alternatively, the concentration of glucose or other osmotic agent may be calculated as an output. Dialysis fluid is a limited resource, as is available time for the complete therapy for the patient. Thus, computer programs typically use a range of possible therapy volumes, i.e., the total volume of dialysis fluid to be used for a particular therapy. A therapy typically includes several cycles, including a fill, a dwell time within the patient's peritoneal cavity, and a drain time. The sum of all the patient fill volumes for each cycle should sum up to the total volume for the therapy. By altering the desired inputs, an optimal therapy for a given patient can then be determined and prescribed, according to the specified outcome(s).

In a custom therapy, on the other hand, dialysis conditions such as glucose concentration and patient kinetic parameters, and dialysis therapy parameters, such as materials and methods, are typically input into the computer, and the outcomes are then calculated. Outcomes may include ultrafiltration volume, urea clearance, and so forth. By changing the input dialysis conditions and parameters, the changes in outcome can be varied and recorded. The therapy can then be adjusted for the desired outcome, and the necessary therapy prescribed.

A patient with an acute or unplanned dialysis need is profoundly different from a typical patient being treated with peritoneal dialysis. With an acute or unplanned need, there is at least a possibility that the kidney function may be restored. There is also at least a possibility that peritoneal dialysis will suffice and that hemodialysis may not be needed at the moment. Hemodialysis may be contraindicated, for example, for a trauma victim. In such a situation, it may be prudent to assume that the patient will benefit from peritoneal dialysis and to spend at least a short period of time to confirm the benefit by initiating peritoneal dialysis.

In such a situation, normal treatment parameters of therapy volume and cycle time should not be considered, because of the urgency of the situation. Thus, very high therapy volumes would not usually be considered because of economic and logistical considerations. Very short cycle times would not ordinarily be considered because the rapid cycling is inconvenient for the patient. In an acute or unplanned situation, however, the patient is in urgent need of dialysis, and for at least a short period of time, it may be beneficial to calculate a therapy in which a dialysis outcome is maximized or optimized, regardless of the total therapy volume or the length of a single cycle. A single cycle includes a fill time, a dwell time, and a drain time. One or more cycles constitute a therapy, e.g., a daily therapy for a patient. In such circumstances, it may also be advisable to ignore for a short period of time other considerations that are otherwise important for the long term survival of the patient. Thus, in an acute or unplanned situation, the therapy temporarily ignore certain outcomes, such as glucose absorption, sodium removal or middle molecule clearances.

Normal parameters for calculating a peritoneal dialysis therapy include practical limits on therapy parameters. Thus, for a simple therapy, available software will accept the desired treatment results and calculate a therapy time, a therapy volume and a cycle time based on typical limits, e.g., a therapy of 9 to 10 hours including 4 to 7 cycles, using 10 to 16 liters of dialysis fluid, and cycle times that include at least an hour or two of dwell time. Of course, a therapy time or other variables may also be specified at the start and used as an input parameter. It has now been unexpectedly discovered, using a standard three-pore model, that very short cycle times and higher dialysate volumes may help improve peritoneal dialysis outcomes. These outcomes include greater ultrafiltration volumes and higher clearance rates of small-molecule solutes from the peritoneum of the patient. Thus, in calculating a peritoneal dialysis therapy, it may be desirable to perform the calculation without regard to the total therapy volume or the cycle times used.

Figure 4:
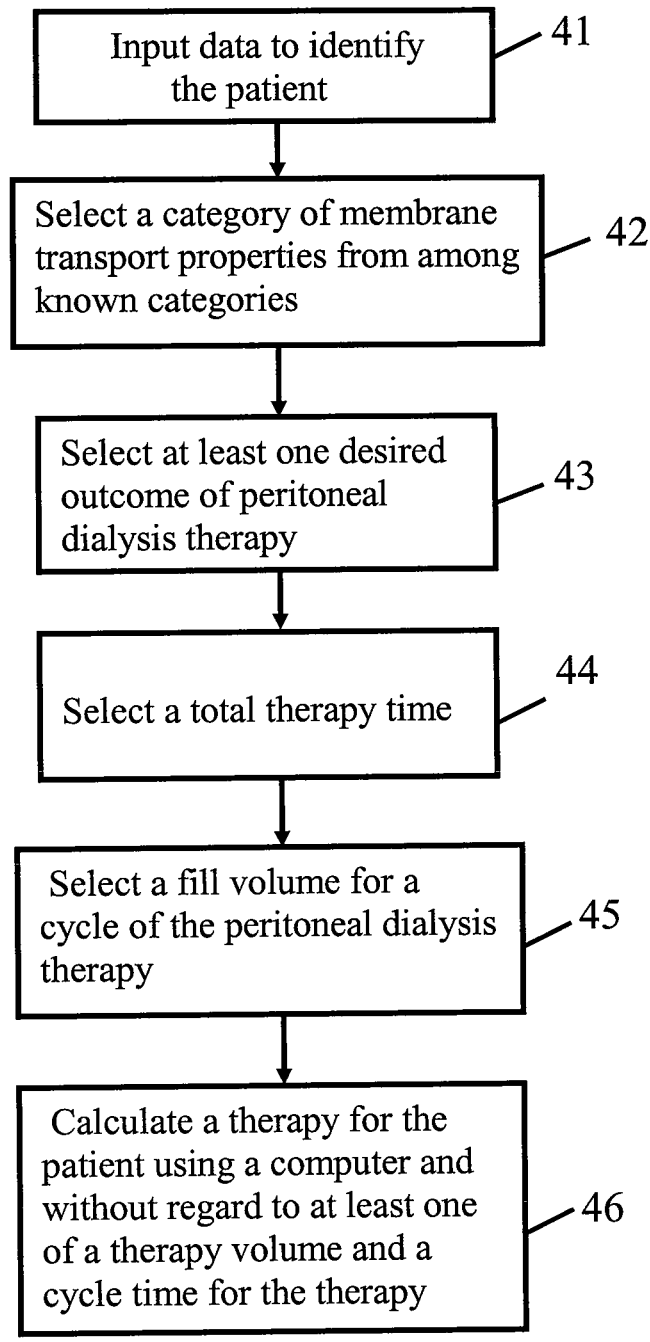
FIGS. 4 and 5 are flowcharts for methods of calculating a peritoneal dialysis therapy.
Figure 5:
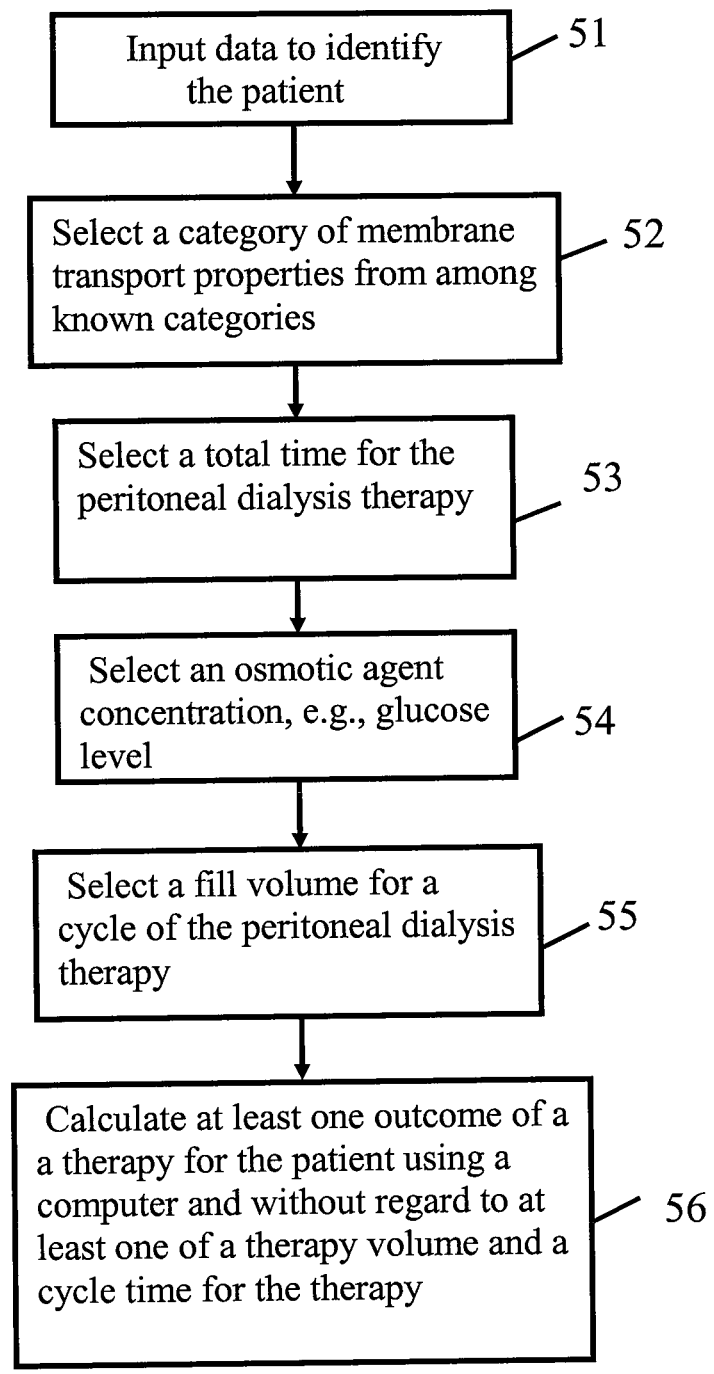

FIGS. 4 and 5 depict flowcharts for methods of performing these calculations, in all of which a digital computer is very useful. FIG. 4 depicts a method for calculating an optimal therapy, in which desired outcomes are used to determine a therapy. Data concerning a patient are input 41, the data including, for example, a patient identifier, a patient age, a previous PET evaluation if available, and other pertinent medical or diagnostic information. If the patient's membrane transport category is known, it may be input or a category selected 42 from among a group of accepted categories. Alternatively, a default category, such as a high transporter may be used.

Desired therapy outcomes are then entered or selected 43. These may include a therapy ultrafiltration volume, a urea or creatinine clearance, and so forth. In this embodiment, a total therapy time is also entered or selected 44. In other embodiments, a concentration of glucose or other osmotic agent may be used as an input parameter, since dialysis fluid is commercially available with only a few osmotic agents and in only a few glucose concentrations. A fill volume suitable for the patient is then selected or entered 45. The software then calculates 46 a therapy for the patient using a computer and without regard to at least one of a therapy volume and a cycle time for the therapy. Cycle times are thus allowed to vary at will. The therapy volume will be the product of the fill volume multiplied by the number of cycles necessary to achieve the desired outcome.

The flowchart of FIG. 5 depicts how to calculate a custom therapy. In this method, data concerning a patient are input 51, the data including, for example, a patient identifier, a patient age, a previous PET evaluation if available, and other pertinent medical or diagnostic information. If the patient's membrane transport category is known, it may be input or a category selected 52 from among a group of accepted categories. Alternatively, a default category, such as a high transporter, a high-average transporter, low-average transporter or a low transporter may be used. In one embodiment, a total time available or desired for the therapy is entered or selected 53. An osmotic agent concentration 54 is then entered or selected, such as a glucose or dextrose percentage. A fill volume suitable for the patient is then selected or entered 55. The software then calculates 56 therapy outcomes for the patient. These outcomes may include a therapy ultrafiltration volume, a urea clearance, a creatinine clearance, or other desired peritoneal dialysis result.

Figure 6:
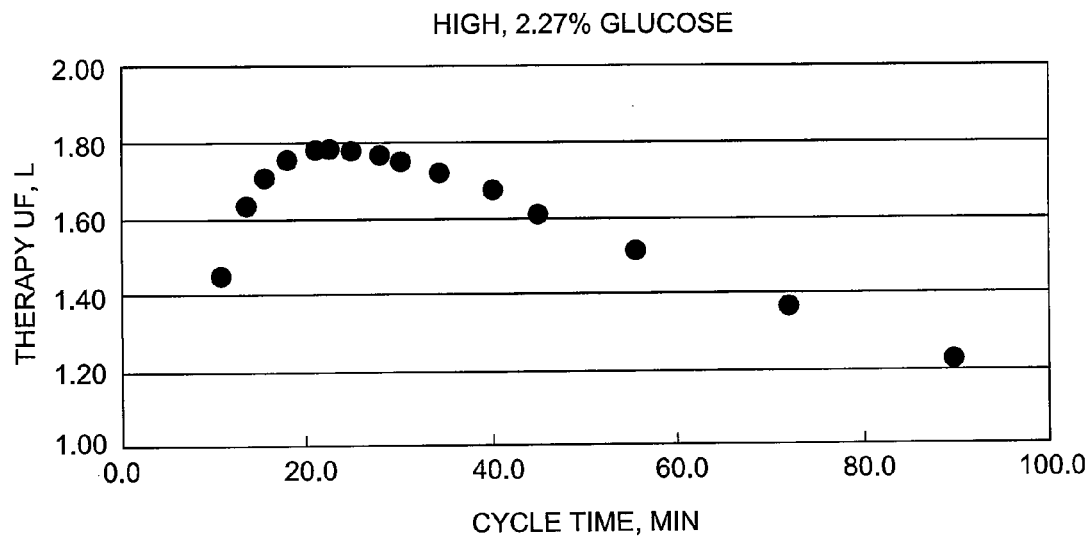
FIGS. 6 to 8 are graphs of calculated dialysis outcomes against dialysis cycle times.
Figure 7:
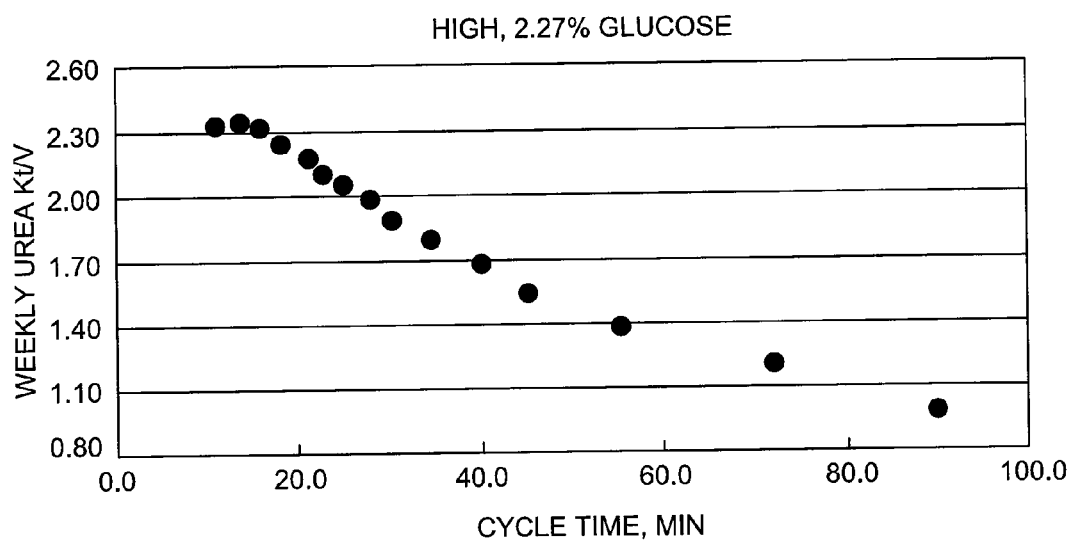

FIGS. 6 and 7 depict test results for calculations using these disclosed methods. FIG. 6 depicts a series of calculations of ultrafiltrate volume for an optimal therapy. FIG. 6 is a graph of cycle time as an independent variable against a calculated resulting ultrafiltration volume in liters for the entire therapy, that is, for the total of all cycles in this particular therapy twelve-hour therapy. In FIG. 6, a series of optimal therapies were calculated using inputs of a high transporter patient, 2.27% glucose dialysis solution, a fill volume of one liter and a therapy time of 12 hours. The program calculated the cycle times in minutes necessary to achieve a total therapy ultrafiltration volume in liters. The greatest ultrafiltration volume for a twelve-hour therapy is reached at a cycle time of about 22 minutes.

This result could also be achieved with a custom therapy calculation, in which a series of desired ultrafiltration volumes, e.g., one to two liters, is used to calculate the needed cycle times, in this case from about 10 to 90 minutes. If the patient has an acute or urgent need, the short cycle times will be preferred, especially those at about 20 to 25 minutes, as shown in FIG. 6. Note that it is not necessary for the patient to have an acute need. These methods may used for any peritoneal dialysis patient with the understanding that these therapies are calculated on the basis of an urgent, short-term need and do not necessarily consider all possibilities, such as increased glucose absorption, potential deficiencies in sodium removal or middle molecule clearances. These therapies also may not include patient considerations, such as the discomfort involved in many short, successive fill and drain cycles and the lifestyle constraints caused by connection to the machine for extended periods to accommodate the many short cycles.

Figure 8:
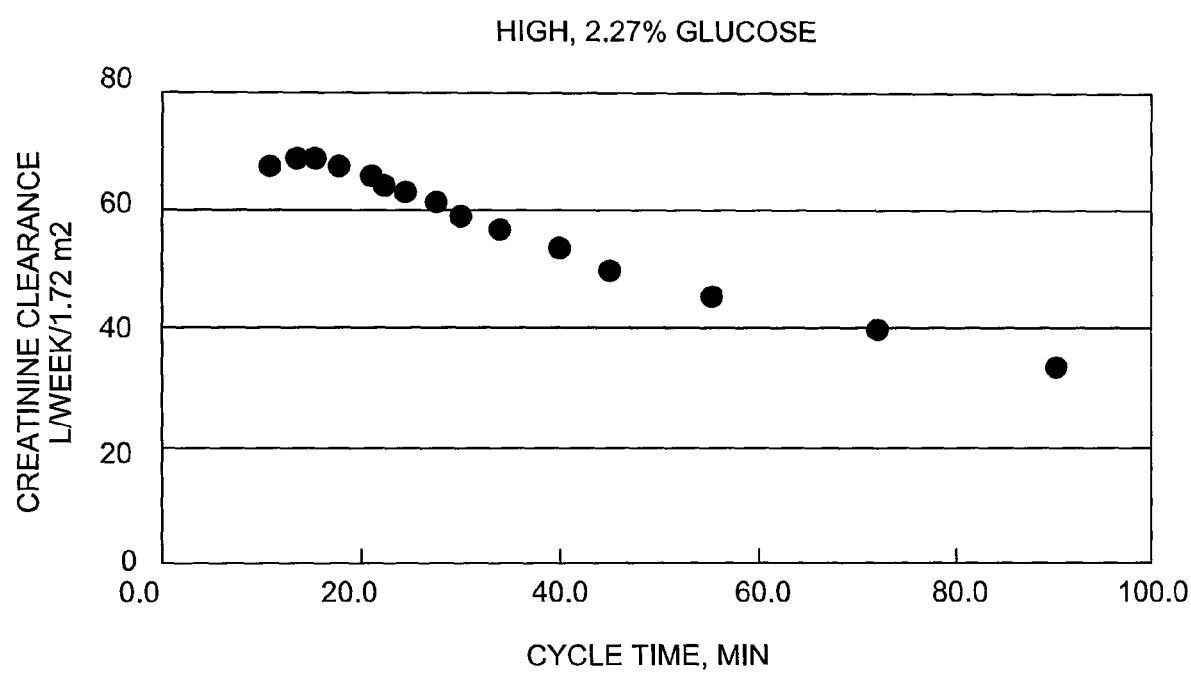

FIG. 7 depicts a graph of weekly urea clearance plotted against the cycle time used for another therapy, still including 2.27% glucose solution. The urea clearance is maximized at a cycle time of about 18 minutes. This result may be achieved with an optimal therapy calculation using a series of the desired clearances as an input and calculating the resulting cycle times. Alternatively, the same result may be achieved in a custom therapy calculation by inputting the possible cycle times and calculating the resultant urea clearances. FIG. 8 depicts similar results for weekly creatinine clearance, with an optimized cycle time, that is, for maximum creatinine clearance, at about 18 minutes. Those having skill in dialysis arts recognize that these cycle times are very short and unexpected, in comparison to typical peritoneal dialysis dwell times and cycle times of hours.

While these results were achieved for helping patients with acute kidney needs, there is no reason to limit the application of these methods only to such patients. Patients with peritoneal membranes having high transport properties will especially benefit from these results. For patients whose transport properties are unknown, peritoneal dialysis may be begun and if favorable results are achieved quickly, the therapy may continue. A standard or other PET test may be performed as desired, if necessary, to confirm that the patient is using the most beneficial therapy.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method of calculating an acute peritoneal dialysis therapy, the method comprising:
inputting data of a patient;
selecting a fill volume for a cycle of the peritoneal dialysis therapy;
selecting at least one therapy parameter or at least one desired outcome of the peritoneal dialysis therapy; and
calculating a therapy for the patient using a digital computer, the patient data, the fill volume and the selected at least one therapy parameter or desired outcome, wherein the digital computer calculates the therapy for the patient without regard to (i) a total therapy volume limit and (ii) a minimum cycle time.

2. The method of claim 1, the cycle time comprising a fill time, a dwell time and a drain time.

3. The method of claim 1, wherein the step of calculating produces a plurality of therapies for the patient, the plurality of therapies comprising a series of cycle times corresponding to a series of values of the at least one desired outcome of the therapy.

4. The method of claim 1, wherein the step of calculating produces a plurality of therapies for the patient, the plurality of therapies comprising a series of therapy volumes corresponding to a series of the at least one desired outcome of the therapy.

5. The method of claim 1, wherein the at least one desired outcome is selected from the group consisting of an ultrafiltration volume, a concentration of a solute in spent dialysis fluid, a solute clearance, and a concentration of a solute in blood of the patient.

6. The method of claim 1, wherein the at least one therapy parameter is selected from the group consisting of an osmotic agent concentration, a patient kinetic parameter or transport category, and a therapy time.

7. The method of claim 1, wherein the at least one therapy parameter comprises a series of cycle times and wherein the step of calculating produces a series of outcomes of the dialysis therapy.

8. A computer program on a computer readable medium for calculating an acute peritoneal dialysis therapy, the computer program comprising:
logic for accepting input data for a patient;
logic for accepting a fill volume for a cycle of the peritoneal dialysis therapy;

logic for accepting an input of at least one therapy parameter or an input of at least one desired outcome of the peritoneal dialysis therapy; and logic for calculating a therapy for the patient using a digital computer, the patient data input, the fill volume and the at least one therapy parameter input or desired outcome, wherein the digital computer calculates the therapy for the patient without regard to (i) a total therapy volume limit and (ii) a minimum cycle time.

9. The computer program according to claim 8, the cycle time comprising a fill time, a dwell time and a drain time.

10. The computer program of claim 8, wherein the logic for calculating includes logic for calculating a plurality of therapies for the patient, the plurality of therapies comprising a series of cycle times or a series of therapy volumes corresponding to a series of outcomes of the therapy.

11. The computer program of claim 8, wherein the logic for accepting an input of at least one therapy parameter includes logic for accepting at least one of an osmotic agent concentration, a patient kinetic parameter or transport category, and a therapy time.

12. A method for calculating an acute peritoneal dialysis therapy, the method comprising:
   inputting data of a patient;
   selecting at least one input parameter for the peritoneal dialysis therapy;
   selecting a fill volume for a cycle of the peritoneal dialysis therapy; and
   calculating at least one peritoneal dialysis therapy including at least one outcome of the therapy for the patient using a digital computer, wherein the digital computer calculates the at least one peritoneal dialysis therapy without regard to (i) a total therapy volume limit and (ii) a minimum cycle time.

13. The method of claim 12, wherein the at least one peritoneal dialysis therapy that is calculated comprises: (i) a therapy volume and (ii) a cycle time or a number of cycles.

14. The method of claim 12, wherein the step of selecting at least one input parameter comprises selecting a series of cycle times for the therapy, and wherein the step of calculating calculates a series of therapy volumes and a series of therapy outcomes.

15. The method of claim 12, further comprising selecting at least one therapy volume for the therapy, wherein the step of calculating calculates a series of cycle times for the therapy and a series of therapy outcomes.

16. The method of claim 12, wherein the at least one outcome of the therapy is selected from the group consisting of an ultrafiltration volume, a concentration of a solute in spent dialysis fluid, a solute clearance, and a concentration of a solute in blood of the patient.

17. The method of claim 12, wherein the at least one input parameter is selected from the group consisting of a total time for the therapy, a total volume for the therapy, an osmotic agent concentration and a cycle time.

18. A computer program on a computer readable medium for calculating an acute peritoneal dialysis therapy, the computer program comprising:
   logic for accepting input data for a patient;
   logic for selecting at least one input parameter for the peritoneal dialysis therapy;
   logic for accepting a fill volume for a cycle of the peritoneal dialysis therapy; and
   logic for calculating at least one peritoneal dialysis therapy including at least one outcome of the therapy for the patient using a digital computer, wherein the digital computer calculates the at least one peritoneal dialysis therapy without regard to (i) a total therapy volume limit and (ii) a minimum value for a cycle time.

19. The computer program according to claim 18, wherein the logic for calculating includes logic for calculating a plurality of therapy outcomes and a plurality of cycle times, wherein a cycle time comprises a fill time, a dwell time and a drain time.

20. The computer program of claim 18, wherein the logic for calculating includes logic for calculating a plurality of therapies for the patient, the plurality of therapies comprising a series of cycle times or volumes corresponding to at least one series of outcomes of the therapy.

\* \* \* \* \*

UNITED STATES PATENT AND TRADEMARK OFFICE
CERTIFICATE OF CORRECTION

| | | |
|---|---|---|
| PATENT NO. | : 8,926,551 B2 | Page 1 of 1 |
| APPLICATION NO. | : 12/498853 | |
| DATED | : January 6, 2015 | |
| INVENTOR(S) | : Lo et al. | |

It is certified that error appears in the above-identified patent and that said Letters Patent is hereby corrected as shown below:

In the Claims:

In column 13, line 19, insert the word --the-- before the phrase --at least--.

Signed and Sealed this
Twenty-sixth Day of May, 2015

Michelle K. Lee
*Director of the United States Patent and Trademark Office*